(12) United States Patent
Hu

(10) Patent No.: US 7,769,429 B2
(45) Date of Patent: Aug. 3, 2010

(54) METHOD AND DEVICE FOR IMPINGEMENT DETECTION

(75) Inventor: Qingmao Hu, Singapore (SG)

(73) Assignee: AO Technology AG, Chur (CH)

( * ) Notice: Subject to any disclaimer, the term of this patent is extended or adjusted under 35 U.S.C. 154(b) by 826 days.

(21) Appl. No.: 10/336,693

(22) Filed: Jan. 6, 2003

(65) Prior Publication Data
US 2003/0176783 A1    Sep. 18, 2003

Related U.S. Application Data

(63) Continuation of application No. PCT/CH00/00372, filed on Jul. 6, 2000.

(51) Int. Cl.
*A61B 5/05* (2006.01)
(52) U.S. Cl. .................. 600/426; 600/424; 600/437
(58) Field of Classification Search .......... 600/416, 600/417, 425–429, 407, 424; 606/130; 702/152, 702/153
See application file for complete search history.

(56) References Cited

U.S. PATENT DOCUMENTS

| | | | |
|---|---|---|---|
| 5,138,553 A | * | 8/1992 | Lanza et al. ............. 600/407 |
| 5,682,886 A | * | 11/1997 | Delp et al. ............. 600/407 |
| 5,715,836 A | | 2/1998 | Lundt et al. |
| 6,266,552 B1 | * | 7/2001 | Slettenmark ............. 600/424 |
| 6,285,902 B1 | * | 9/2001 | Kienzle et al. ............. 600/427 |
| 6,498,944 B1 | * | 12/2002 | Ben-Haim et al. ......... 600/407 |
| 6,801,801 B1 | * | 10/2004 | Sati ....................... 600/429 |

FOREIGN PATENT DOCUMENTS

| | | |
|---|---|---|
| WO | WO 98/38919 | 9/1998 |
| WO | WO 99/16352 | 4/1999 |
| WO | WO 99/23956 | * 5/1999 |
| WO | WO 99/60939 | 12/1999 |

* cited by examiner

*Primary Examiner*—Brian Casler
*Assistant Examiner*—Jonathan G Cwern
(74) *Attorney, Agent, or Firm*—Jones Day

(57) ABSTRACT

Determining impingement between first and second bodies by determining a spatial relationship between surface points of the first body and markers of a first reference element; determining a spatial relationship between surface points of the second body and markers of a second reference element; displacing the first and second bodies relative to the other body; determining 3D coordinates of the respective pluralities of markers; and using at least (1) the 3D coordinates of the respective pluralities of markers of the reference elements, (2) the determined relationship between surface points of the first body and markers of the first reference elements, and (3) the determined relationship between surface points of the second body and markers of the second reference elements, to determine whether a surface point of one of the first and second bodies coincides with a surface point of the other body.

16 Claims, 1 Drawing Sheet

METHOD AND DEVICE FOR IMPINGEMENT DETECTION

RELATED APPLICATIONS

This application is a national stage application of international application No. PCT/CH00/00372, filed 6 Jul. 2000 and incorporated herein by reference in its entirety.

FIELD OF THE INVENTION

The invention relates to a method for determining the presence of impingement between at least first and second bodies. At least one of the first and second bodies may be a medical implant or a portion of a patient's anatomy, such as a bone.

BACKGROUND OF THE INVENTION

For simulation in computer aided surgical interventions the detection of impingement between parts of the patient's anatomy and/or implants is often of key importance. Impingement (collision) detection methods used in the existing literature seem to be unsuitable for two reasons. First, a polyhedral approximation of an anatomical model is not appropriate, since medical images are quite irregular and are essentially non-linear. Secondly, geometric and temporal coherences are not always available, since just final results may be of interest.

A method for performing surgery on a body portion with the steps of loading previously established surgical plan data into a computer, registering a three-dimensional computer model of the body portion stored in the surgical plan data to the body portion of the patient, providing at least one surgical tool, positioning the surgical tool relative to the body portion and performing the surgery is known from U.S. Pat. No. 5,682,886 to Delp. Before the surgical procedure may be effected image data of the body portion must be gathered by means of applying a radiant energy means e.g. magnetic resonance imaging, X-ray devices or computed tomography imaging devices. The so gathered image data is then stored in a memory means for storing image data and the stored image data read into a computer interfaced to the memory means, whereby the computer has a visual display means for displaying images generated in at least one process step.

The surgery plan data comprises the three-dimensional computer model of the body portion and data relating to at least one prosthesis of defined size and position relative to the body. Before performing the surgery the three-dimensional computer model of the body portion is registered on-site to the actual body-portion by means of suitable magnetic devices, acoustic devices or optical devices such as a wand with LED's that are sensed by external cameras.

Furthermore, this known surgical procedure subsystem allows the surgeon to implement the preoperative plan by accurately guiding the placement of the prosthesis on the patient's bone. Thereby, the position measurement device reports to the computer the three-dimensional position of a movable probe, surgical instrument or component of a prosthesis. In case a MR imaging machine (Magnetic Resonance) is used data points are automatically collected in order to register the body portion and the instruments to the three-dimensional computer model. The use of such a MR imaging machine provides the surgeon a real-time image of the body portion and the instruments. Instead of a MR imaging machine a intraoperative CT device (computer tomography) could be used.

This method has the disadvantage that the impingement of two bodies e.g. the body portion and a surgical instrument may only be detected in real-time by using an imaging device, e.g. a MR imaging machine intraoperatively.

SUMMARY OF THE INVENTION

One aspect of the invention relates to a method for determining the presence of impingement between at least two bodies. One embodiment of the method includes acquiring three-dimensional image data of the at least two bodies (1; 2), e.g., as a first set of binary data with reference to at least one three-dimensional system of coordinates. An image acquisition device, such as an x-ray device or ultrasound device may be used to obtain the image data. A second set of data of points, e.g., binary data, on the three-dimensional surface of each of the bodies may be obtained. The second set of data may be with reference to at least one three-dimensional system of coordinates and may be obtained using the first set of binary data acquired.

Each of the bodies is associated with a reference element comprising a respective plurality of markers. A mathematical relationship is determined between the at least one three-dimensional system of coordinates and the position of the markers rendering possible a relationship between the points on the surface of the bodies and the markers.

At least one of the bodies is displaced relative to the other.

Upon displacement, three-dimensional coordinates of the markers with respect to an on-site three-dimensional system of coordinates are determined. A position measuring device, such as one comprising a plurality of cameras may be used to determine the coordinates of the markers.

The three-dimensional coordinates of the markers may be transformed into three dimensional coordinates of the surface points of the bodies with respect to the onsite three-dimensional system of coordinates. Preferably, the method further comprises determining, such as by computer, whether at least a surface point of one of the bodies and a point of the other body being closest to each other coincide within the on-site three dimensional system of coordinates. The determination of impingement is preferably performed using a fast impingement detection algorithm.

A preferred fast impingement detection algorithm comprises a) obtaining the surface representations of the bodies; b) defining a linear transformation to calculate spatial indices of points of the bodies; and c) constructing a lookup table to confine free space where impingement may occur. The lookup table may comprise an array of binary values, with 0 representing free spatial positions and 1 representing occupied positions. The entries to the lookup table may be spatial indices. The space defined by the lookup table is searched to determine the presence of impingement.

The first set of data may comprise a three dimensional array of voxels, e.g., binary voxels or bitvolumes. The voxels may be generated by segmenting and reconstructing a computer aided tomography image. A medical imaging library may be used to receive and optionally store the first set of data.

At least one of the bodies may be a surgical implant. At least one of the bodies may be a portion of a patient's anatomy, e.g., a bone or portion thereof.

Another aspect of the invention relates to a device for determining the presence of impingement between at least two bodies. The device preferably includes at least two reference elements each comprising a respective plurality of markers, e.g., at least 3 nonlinearly arranged markers. The reference elements are preferably attachable to the at least two bodies. For example, each reference element may comprise a screw that may be associated, such as by threading, with a bone, bone fragment or surgical implant. The device preferably includes a position measurement device configured to determine three dimensional coordinates of the markers of the reference elements. A computer is preferably connected with the position measurement device and may be provided with software configured to determine the position of the markers with reference to an on-site three-dimensional coordinate system. The device preferably includes an indicator configured to to indicate the presence of impingement between the two bodies.

For example, the indicator may be configured to generate a visual or audio indicator of impingement. Thus, the device may comprise speakers and a voice coder associated with the computer to indicate the presence of impingement through speech.

BRIEF DESCRIPTION OF THE DRAWINGS

The present invention is discussed below in reference to the drawings, in which.

DETAILED DESCRIPTION OF THE INVENTION

Figure 1:
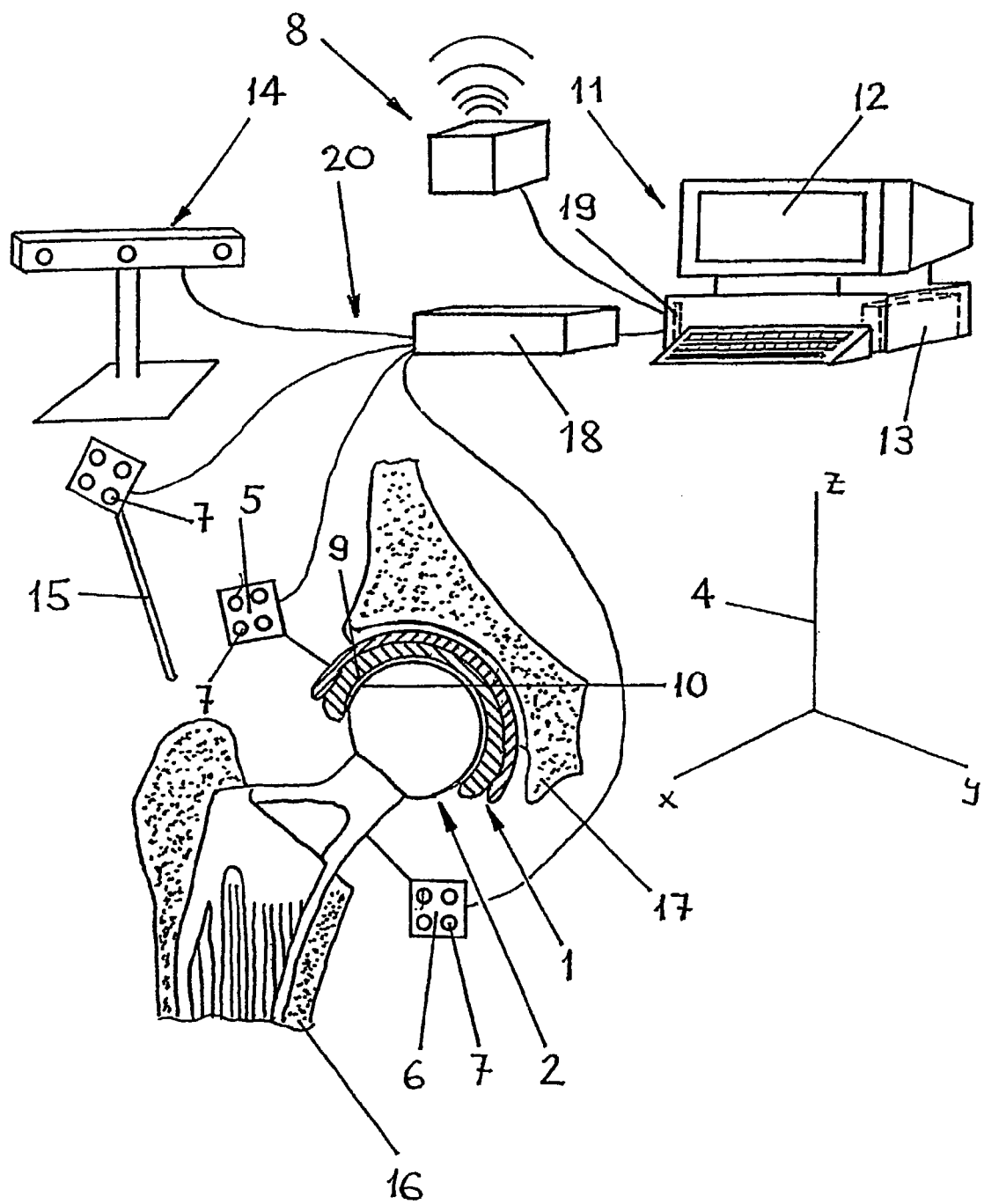
FIG. 1: shows the preferred embodiment of the device according to the invention with a femoral and acetabular components of a total hip prosthesis as first and second body.

One aspect of the present invention relates to a method to detect impingement between two bodies, preferably in real-time, by using registration devices and without the need of intraoperative imaging as MR, CT or X-ray devices.

By determining the presence of impingement, the present invention provides a method for determining when a geometric contact between two bodies has or is about to occur. The problem of determining the presence of impingement may be encountered in computer-aided design and machining (CAD/CAM), robotics and automation, manufacturing, computer graphics, animation, and computer simulated environments. [5] In many of these application areas, collision detection is a major computational bottleneck.

There are two types of collision detection methods. A first type determines whether the surfaces of objects intersect [6], while the second type is based on the calculation of distances of objects, since two objects are separate if they have a positive distance from each other [4]. These methods always suppose that objects are represented or approximated as polyhedrons [8], which representation is not always feasible in anatomic-related applications, where the objects are some anatomical parts and are essentially non-linear. These methods need to perform a search for closest feature pairs, or a calculation of dot products of vectors of all polygons and edges, which is quite time consuming when models are non-linear. In addition, these methods suppose that objects move only slightly between successive time steps or simulation frames, so that temporal and geometric coherences [5] play a crucial role to speed up the calculation. This assumption is not always true in computer aided surgery if, for example, the range of motion of the femur with respect to pelvis [2] must be calculated.

The collision detection problem in computer aided surgery can be better described by applying a relative transformation to an anatomical object and checking if collision occurs, since the status of intermediate positions may be considered clinically irrelevant. In addition, the more general term 'collision' is referred to as impingement in medically related applications [2], and the research effort so far has been quite limited. Unlike in other applications, where the geometric models are explicitly given in the form of polygonal objects, splines, or algebraic surfaces, the anatomical medical image is rather irregular, and implicit geometric models are preferred. Physically, bony objects cannot penetrate one another. Therefore it is not necessary to compute the exact volume of penetration, rather it will suffice to report if and where impingement between the objects occurs.

A detailed description of methods for generating a medical image data set as a three dimensional array of binary voxels (bitvolumes) through segmentation and reconstruction of a medical image received e.g. via a radiant energy means can be found in [12]. Suitable methods medical imaging technologies for use with the present invention include X-ray, Magnetic Resonance Imaging (MR), Computed Tomography, Positron Emission Tomography (PET), Single Photon Emission Computing Tomography (SPECT) and Ultrasonography. Another suitable method of gathering three-dimensional image data of the two bodies as a first set of binary data comprises the use of Computer Aided Design Software on a computer.

For computing if and where two surface points being each on the surface of separate body and being closest to each other coincide within the on-site three-dimensional system of coordinates is preferably performed through a fast impingement detection algorithm allowing the performance of the method according to the invention in real time.

The preferred algorithm of the method according to the invention takes implicit object models from reconstruction of anatomical CT data that represent complicated anatomical structures. To speed up the detection procedure, a lookup table and a linear transformation may be introduced. Searching for impingement between any two objects thus may be accomplished by calculating spatial indices and searching the lookup table. Thereby it is preferably assumed that all objects are rigid bodies, i.e. they do not undergo any deformations.

Determining the presence of impingement among multiple objects can be represented as impingement detection between groups of two objects. Thus, the present method for determining impingement between at least two objects is suitable for determining the presence of impingement between objects of a plurality of objects.

If two objects impinge, i.e., collide, the objects must share at least one common point in space. Both objects are free to move in space, but in fact, the problem can be modeled as the relative movement of one object with respect to the other one. When two objects change their relative positions in a way that contact occurs, the first contact point is located on the surfaces of both objects. Except for one special case, which is discussed later in this section, two objects must have at least one common surface point when they impinge. Since the number of surface points of an object is much smaller than the number of voxels making up the object, it is more efficient to search for impingement only among the surface points. The proposed algorithm can be broken into the following steps: (a) obtaining the surface representations of objects, (b) defining a linear transform to calculate the spatial indices, (c) building up a lookup table to confine the free space where impingement may occur, and (d) searching the confined space to locate possible impingement. These steps are discussed in detail in the following.

(a) Suppose two objects A and B are given as three dimensional arrays of binary voxels, so-called bitvolumes. Without losing generality, it can be assumed that A is static, and B may move with respect to A. This assumption is valid since only relative movement needs to be considered. Surface representations of both objects can be obtained by segmentation and reconstruction of the associated CT data. This creates only the bitvolumes, not the surfaces. The process of segmentation is known and need not be discussed herein.

Suppose that the number of surface points of A is $L_A$ and that of B is $L_B$. The coordinates of the i-th surface boundary point of A and B are given by $$(X_A(i), Y_A(i), Z_A(i)), (i=1, 2, \ldots, L_A),$$

$$(X_B(i), Y_B(i), Z_B(i)), (i=1, 2, \ldots, L_B).$$

Let us denote the maximum and minimum values of $X_A(i)$, $Y_A(i)$, $Z_A(i)$ by $Max_A X$ and $Min_A X$, $Max_A Y$ and $Min_A Y$, and $Max_A Z$ and $Min_A Z$, respectively. Mathematically these relationships are given by:

$$Min_A X \leq X_A(i) \leq Max_A X (i=1, 2, \ldots, L_A)$$

$$Min_A Y \leq Y_A(i) \leq Max_A Y (i=1, 2, \ldots, L_A)$$

$$Min_A Z \leq Z_A(i) \leq Max_A Z (i=1, 2, \ldots, L_A) \quad (1)$$

From equation (1) the three-dimensional extent of A along each axis can be calculated:

$$Dim_A X = Max_A X - Min_A X$$

$$Dim_A Y = Max_A Y - Min_A Y$$

$$Dim_A Z = Max_A Z - Min_A Z \quad (2)$$

(b) A linear transform can be performed to define a spatial index id (x, y, z) for a given point (x, y, z):

$$id(x, y, z) = x - Min_A X + (y - Min_A Y)(Dim_A X + 1) + (z - Min_A Z) \cdot (Dim_A X + 1) \cdot (Dim_A Y + 1) \quad (3)$$

where (x, y, z) satisfy equation (1). This index is used to quickly access elements in the LUT defined below. From a given index id (x, y, z), the spatial point (x, y, z) can also be uniquely calculated:

$$z = \text{int}\left[\frac{id}{(Dim_A X + 1)(Dim_A Y + 1)}\right] + Min_A Z \quad (4)$$

$$y = \text{int}\left[\frac{id - (z - Min_A Z)(Dim_A X + 1)(Dim_A Y + 1)}{Dim_A X + 1}\right] + Min_A Y \quad (5)$$

$$x = id - (z - Min_A Z)(Dim_A X + 1)(Dim_A + 1) - (y - Min_A Y)(Dim_A X + 1) + Min_A X \quad (6)$$

where int [f] is a function that gives an integer value $f_i$ for a real variable f with $f_i \geq f$ and $(f_i - f) < 1$. From equations (3)-(6), a one-to-one relationship between spatial points and their spatial indices can be created to map equivalence. This equivalence allows one to search the lookup table (LUT, defined below) in order to determine if two objects share any spatial positions.

(c) A one-dimensional lookup table (LUT) is created. It is based upon the spatial information of the static object A. The size of the look-up table is given by:

$$SIZE = (Dim_A Z + 1) \cdot (Dim_A Y + 1) \cdot (Dim_A X + 1)$$

Initially, the LUT (id (x, y, z)) is initialized to 0 for all points, since no impingement initially occurs. Then, for every surface boundary point of A $(X_A(i), Y_A(i), Z_A(i))$, the spatial index $$id(X_A(i), Y_A(i), Z_A(i))(i))(i=1, 2, \ldots, L_A)$$

is calculated, and LUT (id $(X_A(i), Y_A(i), Z_A(i))$) is set to a non-zero value to represent that this spatial position is occupied by object A.

(d) After any relative movement of B with respect to A, the coordinates of the i-th surface point of B are calculated or computed as $$(TX_B(i), TY_B(i), TZ_B(i))(i=1, 2, \ldots, L_B)$$

If the relative transformation of B with respect to A can be expressed as a rotation matrix R and a translation vector T, then $(TX_B(i), TY_B(i), TZ_B(i))$ are calculated from $(X_B(i), Y_B(i), Z_B(i))$, by the following formulae, $$TX_B(i) = R[0][0]*X_B(i) + R[0][1]*Y_B(i) + R[0][2]*Z_B(i) + T[0] \quad (7)$$

$$TY_B(i) = R[1][0]*X_B(i) + R[1][1]*Y_B(i) + R[1][2]*Z_B(i) + T[1] \quad (8)$$

$$TZ_B(i) = R[2][0]*X_B(i) + R[2][1]*Y_B(i) + R[2][2]*Z_B(i) + T[2] \quad (9)$$

for all points $(TX_B(i), TY_B(i), TZ_B(i))$ satisfying:

$$Min_A X \leq TX_B(i) \leq Max_A X$$

$$Min_A Y \leq TY_B(i) \leq Max_A Y$$

$$Min_A Z \leq TZ_B(i) \leq Max_A Z$$

the spatial index id $(TX_B(i), TY_B(i), TZ_B(i))$ can be calculated according to (3). If LUT (id $(TX_B(i), TY_B(i), TZ_B(i))$) is zero, for all i=1, 2, ..., $L_B$, none of B's surface points is located at a position that is occupied by one of A's surface points, which means the absence of impingement. If however, for one i, LUT (id $(TX_B(i), TY_B(i), TZ_B(i))$) is non-zero, A and B share a common surface point at $(TX_B(i), TY_B(i), TZ_B(i))$, which means that impingement has occurred. All points $(TX_B(i), TY_B(i), TZ_B(i))$ with LUT (id $(TX_B(i), TY_B(i), TZ_B(i))$) non-zero are deemed to be contact points of the impingement.

Theoretically, there is one special case of impingement that needs to be mentioned, i.e. the case when object B is totally enclosed within object A. Although impingement does occur, there are no shared surface points, and hence the proposed algorithm will fail. To account for this exception, the described algorithm is slightly modified. Instead of representing the static object A by its surface, A is represented by its entire volume, and LUT is set to non-zero values for all voxels of A. When impingement occurs, the surface points of object B are checked against the modified LUT, which resolves the described pathologic case. However, since this exception can never occur physically, the basic algorithm may be used for testing and verification.

The determination of the coordinates of the markers attached to the reference bodies with respect to the three-dimensional on-site coordinate system is performed with a position measurement device that is connected to the computer using software to evaluate the coordinates from the data received from the position measurement device.

The markers as well as the detectors of the position measurement device may be acoustic or electromagnetic devices, such as energy emitters, receivers, or reflectors. For instance as energy emitters, light sources, particularly light emitting diodes (LED's); infrared light emitting diodes (IRED's); acoustic transmitters; or coils may be used. For receiving energy from the markers, light detectors, such as cameras or photodiodes, microphones, or Hall-effect components may be used.

A custom optoelectronic position measurement device may be used e.g. an OPTOTRAK 3020 System, Northern Digital, Waterloo, On., Canada. It preferably comprises -an OPTOTRAK 3020 Position Sensor consisting of three one-dimensional chargecoupled devices (CCD) paired with three lens cells and mounted on a stabilized bar.

Within each of the three lens cells, light from an infrared marker is directed onto a CCD and measured. All three measurements together determine-in real time-the three-dimensional location of the marker; -a system control unit; -a computer interface card and cables; -data collection and display software; and -a strober and marker kit. Computer assisted surgery systems (CAS systems) that are provided with a computer and a position measurement device in order to measure the position of surgical instruments or devices which are displaceable within the operation area are disclosed e.g. in U.S. Pat. No. 5,383,454 BUCHHOLZ and EP 0 359 773 SCHLONDORFF. Often these CAS-systems comprise a memory means in order to store medical images such as e.g. X-rays, Computertomographs or MR images (Magnetic Resonance images) using radiant energy means. Thereby the medical images may be gathered pre-operatively or intraoperatively.

A key issue in computer assisted surgery (CAS) is to establish a mathematical relationship between the patient's intra-operative position respectively the on-site position of the surgical implants and the three-dimensional computer model of the patient's body respectively the surgical implants that are stored e.g. as a data set in a medical imaging library. The process of computing a transformation from coordinates within an on-site coordinate system to image coordinates is referred to as "registration" or "matching". Recent developments allow the surgeon to obtain a number of points on the surface of a bone or implant with a pointer having at least three markers and measure the position of the pointer with the position measurement device whereby this "cloud of points" can be mathematically fit onto the medical image of the bone surface or implant surface through an optimization algorithm [9; 10]. This process is termed "surface matching". A suitable method for determining points using a pointer is described in application Ser. No. 09/562,951, filed May 3, 2000, now U.S. Pat. No. 6,801,801. Instead of using a pointer an ultrasound device may be used in order to gather a number of points on the surface of a bone or implant. A suitable method and ultrasound device are disclosed in application Ser. No. 09/968,822, filed Oct. 2, 2001, now U.S. Pat. No. 6,605,041.

The device for impingement detection between at least two bodies according to the invention comprises: A) at least two reference bodies each having at least three non-linearly arranged markers attachable to two bodies, particularly to bones, bone fragments or surgical implants; B) a position measurement device in order to determine the on-site position of the markers; C) a computer connected to the position measurement device and provided with software apt to compute the position of the markers with reference to an on-site three dimensional coordinate system; and D) indicating means indicating the occurrence of impingement between the two bodies.

In a preferred embodiment of the device according to the invention the indicating means consist of an alarm.

In another embodiment of the device according to the invention the alarm preferably comprises loudspeakers and a voice coder connected to the computer to indicate the occurrence of impingement through speech. Further advantageous of the invention are stated in the dependent claims.

Advantages of the method according to the invention include:—A minimal invasive surgical technique may be applied e.g. during implantation of prostheses;—The algorithm provides a general-purpose impingement detection method in the sense that the objects (bodies, bone fragments) can be of any shape; and—It can be extended to any number of objects in the scene.

Referring to FIG. 1, an exemplary application of the device according to the invention is shown in reference to a total hip replacement operation. The device comprises two reference elements 5,6 with markers 7, e.g., four LED's, that are attached to the two bodies 1;2. In FIG. 1, body 1 is an acetabular component and body 2 is a femoral component of a total hip prosthesis which attach to the acetabulum 17 and femur 16 of a patient. An opto-electronic position measurement device 14 is used to determine coordinates of the markers 7 within the on-site three-dimensional system of coordinates. The device 14 comprises a system control unit 18 and cables 20.

A computer 11 preferably includes a display monitor 12, a display data storage 13 and a computer interface card 19 to connect the computer 11 to the position measurement device 14.

A pointer 15 comprises markers 7 and may be used to perform a registration step by obtaining coordinates of a number of surface points.

An indicator 8 may be a visual or audio alarm for indicating the presence of impingement between surface points 9,10 that are respectively associated with the surface of body 1 and body 2. The points 9,10 may be the closest points to each other of the respective bodies. The computation of this impingement detection may be performed by means of the computer 11.

All references cited herein are incorporated herein by reference in their entirety and for all purposes to the same extent as if each individual publication or patent or patent application was specifically and individually indicated to be incorporated by reference in its entirety for all purposes.

Many modifications and variations of this invention can be made without departing from its spirit and scope, as will be apparent to those of skill in the art. The specific embodiments described herein are offered by way of example only, and the invention is to be limited only by the terms of the appended claims, along with the full scope of equivalents to which such claims are entitled.

REFERENCES

1. Gong J, B chler R, Sati M, Nolte L P (1997) Restricted surface matching: a new approach to registration in computer assisted surgery. In In Troccaz J, Grimson E, Moesges R (Eds.): First Joint Conference Computer Vision, Virtual Reality and Robotics in Medicine and Medical Robotics and Computer Assisted Surgery. Grenoble, France. Springer 597-605
2. Jaramaz B, Nikou C, Simon D A, DiGioia A M (1997) Range of motion after total hip arthroplasty: experimental verification of the analytical simulator. In Troccaz J, Grimson E, Moesges R (Eds.): First Joint Conference Computer Vision, Virtual Reality and Robotics in Medicine and Medical Robotics and Computer Assisted Surgery. Grenoble, France. Springer 573-582
3. Lin M C, Canny J F (1991) A fast algorithm for incremental distance calculation. Proceeding of IEEE International Conference on Robotics and Automation, Calif., USA, 2: 1008-1014 4. Lin M C (1993) Efficient collision detection for animation and robotics. Ph. D. thesis. University of California, Department of Electrical Engineering and Computer Science, Berkeley, USA
5. Lin M C, Manocha D (1995) Fast interference detection between geometric models. The Visual Computer 11 (10): 542-561
6. Moore M, Wilhelms O (1988) Collision detection and response for computer animation. Computer Graphics 22(4): 289-298
7. Nolte L P, Zamorano L, Visarius H. Berlemann U, Langlotz F, Arm E, Schwarzenbach O (1995) Clinical evaluation of a system for precision enhancement in spine surgery. Clinical Biomechanics 10 (6): 293-303
8. Zeiller M (1994) Collision detection for complex objects in computer animation. Ph. D. thesis. Technical University of Vienna, Austria
9. Gong, J., B chler, R., Sati, M., Nolte, L. P. Restricted surface matching: A new approach to registration in computer assisted surgery Proc. 3 Int. Symp. Med. Robot. Comput. Assist. Surg. (MRCAS)
10. Bachoter, R., Bunke, H., Nolte, L. P. Restricted surface matching-Numerical optimization and technical evaluation Comput. Aided Surg. 1999
12. Pommert, A., Riemer, M., Schiemann, T., Schubert, R., Tiede, U., Hohne, K. H. Three-dimensional imaging in medicine: methods and applications Pommert et al.: 3D Imaging in Medicine

What is claimed is:

1. A method of determining the presence of impingement between at least first and second bodies, comprising:
    (a) for each of the first and second bodies, obtaining a respective set of data indicative of three-dimensional (3D) coordinates of points of a surface of the body;
    (b) associating a first reference element with the first body and associating a second reference element with the second body, wherein each of the first and second references elements comprises a respective plurality of markers;
    (c) determining a spatial relationship between (1) at least some of the points of the surface of the first body determined in step (a) obtaining and (2) the markers of the first reference element;
    (d) determining a spatial relationship between (1) at least some of the points of the surface of the second body determined in step (a) and (2) the markers of the second reference element;
    (e) displacing at least one of the first and second bodies relative to the other body;
    (f) determining 3D coordinates of the markers of the first and second reference elements; and
    (g) using at least (1) the 3D coordinates of the markers of the first and second reference elements determined in step (f), (2) the spatial relationship determined in step (c), and (3) the spatial relationship determined in step (d), to determine whether a surface point of one of the first and second bodies coincides with a surface point of the other body,
    wherein step (g) comprises (h) defining a transformation to calculate spatial indices for each surface point of the first and second bodies; (i) forming up a lookup table, wherein the lookup table comprises an array of values, a first value representing a free spatial position and a second value representing an occupied spatial position and further wherein the entries to the lookup table are spatial indices determined using the transformation defined in step (h); and (j) searching the lookup table to determine the presence of impingement.

2. The method of claim 1, wherein step (a) comprises acquiring first three-dimensional (3D) image data of the at least first and second bodies and using the first 3D data to obtain the respective sets of data of points of the surface of each body.

3. The method of claim 2, wherein the 3D image data is referenced to at least one 3D system of coordinates.

4. The method of claim 1, wherein step (f) comprises transforming the 3D coordinates of the markers into an onsite system of 3D coordinates, wherein the onsite system of 3D coordinates includes the surface points of the bodies.

5. The method of claim 1, wherein the 3D image data comprises ultrasound image data.

6. The method according to claim 1, wherein the 3D image data comprises x-ray image data.

7. The method of claim 1, wherein the respective sets of data indicative of three-dimensional (3D) coordinates of points of a surface of the body each comprise a three dimensional array of voxels.

8. The method of claim 7, wherein the voxels are bit volumes generated by segmenting and reconstructing a computer aided tomography image.

9. The method of claim 1, wherein at least one of the first and second bodies is a surgical implant.

10. The method of claim 1, wherein at least one of the first and second bodies comprises a portion of a patient's anatomy.

11. The method of claim 10, wherein at least one of the first and second bodies is a bone.

12. A device for determining the presence of impingement between first and second bodies, the device comprising:
    (a) at least two reference elements, each reference element having at least three non-linearly arranged markers and being attachable to one of the first and second bodies;
    (b) a position measurement device configured to determine three dimensional coordinates of the markers of the reference elements; and
    (c) a computer configured to at least (1) determine the position of the markers with reference to an on-site three-dimensional coordinate system, define a transformation to calculate spatial indices for each surface point of the first and second bodies, form up a lookup table, wherein the lookup table comprises an array of values, a first value representing a free spatial position and a second value representing an occupied spatial position and further wherein the entries to the lookup table are spatial indices determined using the transformation and (2) determine the presence of impingement between the two bodies by searching the lookup table.

13. The device of claim 12, further comprising an indicator to indicate to an operator the presence of impingement.

14. The device of claim 13, wherein the indicator comprises a visual indicator or audio indicator.

15. The device of claim 14, wherein the device comprises a sound generating device and a voice coder to indicate the presence of impingement through speech.

16. A device for determining the presence of impingement between first and second bodies, the device comprising:
    (a) at least two reference elements, each reference element having at least three non-linearly arranged markers and being attachable to one of the first and second bodies;
    (b) a position measurement device configured to determine three dimensional coordinates of the markers of the reference elements;
    (c) a computer configured to at least (1) determine the position of the markers with reference to an on-site three-dimensional coordinate system, define a transformation to calculate spatial indices for each surface point of the first and second bodies, form up a lookup table, wherein the lookup table comprises an array of values, a first value representing a free spatial position and a second value representing an occupied spatial position and further wherein the entries to the lookup table are spatial indices determined using the transformation and (2) determine the presence of impingement between the two bodies by searching the lookup table; and
    (d) an indicator providing a visual or audible alarm to an operator to indicate the presence of impingement.

* * * * *